United States Patent [19]

Naylor

[11] Patent Number: 5,120,645
[45] Date of Patent: Jun. 9, 1992

[54] PRODUCTION OF 2-DEOXYURIDINE

[75] Inventor: Linda A. Naylor, Durham, England

[73] Assignee: Imperial Chemical Industries PLC, London, England

[21] Appl. No.: 494,528

[22] Filed: Mar. 16, 1990

[30] Foreign Application Priority Data

Mar. 22, 1989 [GB] United Kingdom ............... 8906624

[51] Int. Cl.⁵ .................. C12N 1/20; C12R 1/13; C12P 19/38; C12P 19/40
[52] U.S. Cl. .................................. 435/87; 435/88; 435/252.1; 435/840
[58] Field of Search ............... 435/87, 88, 252.1, 840

[56] References Cited

U.S. PATENT DOCUMENTS 4,835,104  5/1989  Yokozeki et al. .................... 435/87
4,880,736 11/1989  Tsunemi et al. ....................... 435/87

OTHER PUBLICATIONS

Derwent Abs. 90-031005/05 Naylor EP344937 (Dec. 1989).
Derwent Abs. 86-025474/04 Yamasa Shoyu J60248197 (May 1984).

Primary Examiner—Herbert J. Lilling
Attorney, Agent, or Firm—Cushman, Darby & Cushman

[57] ABSTRACT

A process for the preparation of 2-deoxyuridine, which can be used as a nucleus for compositions useful as therapeutic drugs, in which a strain of the genus Brevibacterium is cultivated on a suitable nutrient medium, e.g. containing glucose as a carbon source. Preferred Brevibacterium strains are strains of *Brevibacterium helvolum* in particular strains NCIMB 40117 and NCIMB 40116 which 2 strains are claimed per se.

8 Claims, No Drawings

PRODUCTION OF 2-DEOXYURIDINE

This invention relates to a process for the production of 2-deoxyuridine and to a novel bacterial strain used in its production.

2-deoxyuridine can be used as a nucleus for compositions useful as therapeutic drugs. It has the structure:

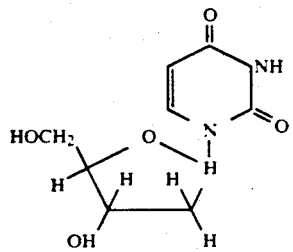

In our published European Patent Application No. 344937 we have described the production of novel Brevibacterium strain NCIMB 40014 from strain ATCC 19390 mentioned in U.S. Pat. No. 3,586,606. NCIMB 40014 can be used in a fermentation process for the production of the deoxyribonucleoside thymidine and/or its corresponding base thymine.

According to the present invention we provide a process for the production of 2-deoxyuridine which comprises aerobically cultivating a 2-deoxyuridine producing bacterial strain of the genus Brevibacterium in a culture medium containing an assimilable carbon source and other nutrients under suitable cultural conditions, accumulating the produced 2-deoxyuridine directly in the medium and thereafter separating the produced and accumulated 2-deoxyuridine from the medium.

Any suitable strain of the genus Brevibacterium may be used in the process of the invention but 2-deoxyuridine producing strains of *Brevibacterium helvolum* are preferred. A particularly suitable strain is strain L-17 derived from *Brevibacterium helvolum* NCIMB 40014 by the method described in detail in Example 1 of this specification. The derivation of strain NCIMB 40014 from strain ATCC 19340 (itself mentioned in U.S. Pat. No. 3,586,606 which describes a process for producing ribotides of 2-substituted-6-hydroxypurines by fermentation) is described in detail in our published European Patent Application No. 344937. A further suitable strain also derived from strain ATCC 19390 is *Brevibacterium helvolum* strain 2.977. Cultures of strains L-17 and 2.977 have been deposited at the National Collections of Industrial and Marine Bacteria Ltd. (NCIMB), 23 St Machan Drive, Aberdeen, AB2 1RY, Scotland, United Kingdom on Feb. 21, 1989 and have been given the accession numbers NCIMB 40117 and NCIMB 40116 respectively. Strain NCIMB 40014 was deposited on Apr. 28, 1988.

Also according to the present invention we provide biologically pure cultures of *Brevibacterium helvolum* strain NCIMB 40117 and *Brevibacterium helvolum* strain NCIMB 40116 and variants and mutants derived from these strains.

The process of the invention is most effective when carried out as a fed batch or batch process but continuous methods are possible. Preferably the carbon source is glucose but other carbon sources such as other sugars and alcohols can be used. Preferably the pH is in the range 5 to 9, particularly 6 to 8 with a pH at or near 7 being especially suitable. A base such as ammonium hydroxide can be added to the culture medium to maintain the pH at the required level. Suitably the temperature is in the range 20° to 35° C. with temperatures in the range 25° to 30° C. being preferred. A very suitable production medium for the process of the invention is set out in Table 1.

TABLE 1

| Component | Concentration per l |
|---|---|
| yeast extract | 10.0 g |
| $MgSO_4.7H_2O$ | 2.0 g |
| $K_2SO_4$ | 2.0 g |
| trisodium citrate.$2H_2O$ | 0.5 g |
| $CaCl_2$ | 0.55 g |
| $FeSO_4.7H_2O$ | 0.1 g |
| $MnSO_4.4H_2O$ | 16.2 g |
| $ZnSO_4.7H_2O$ | 44.0 mg |
| $CuSO_4.5H_2O$ | 8.0 mg |
| $Co(NO_3)_2$ | 0.5 ml |
| Na Molybdate.$2H_2O$ | 1.0 mg |
| Thiamine | 5.0 mg |
| Calcium pantothenate | 10.0 mg |
| Biotin | 1.0 mg |
| Folic acid | 50.0 g |
| $H_3PO_4$ | 50 ml |
| Glucose | To give 150 g |

After production and accumulation of the 2-deoxyuridine it may be separated from the supernatant liquid in the culture by any suitable means for example ion exchange, liquid extraction and hydrophobic chromatography, ion exchange being preferred. A suitable ion exchange separation procedure for 2-deoxyuridine is to adsorb this solute onto an ion exchange resin and to elute the 2-deoxyuridine specifically using water.

The produced 2-deoxyuridine can be used in the production of a number of medical and biochemical drug products.

The invention is illustrated by the following examples:

EXAMPLE 1

Production of Strain L-17

Strain L-17 was produced from strain NCIMB 40014 by treating a culture of strain NCIMB 40014 with 5-fluoro 2-deoxyuridine and selecting those cells which were resistant to high concentrations of this pyrimidine analogue to produce strain L-17. Strain L-17 shows a marked ability to produce 2-deoxyuridine which product accumulates in the culture medium.

EXAMPLE 2

Production of 2-deoxyuridine

The inoculation medium set out in Table 2 was prepared and was inoculated in a shake flask with a culture of strain Brevibacterium L-17 produced as described in Example 1.

TABLE 2

| Component | Concentration per l |
|---|---|
| 0.5M phosphate buffer | 20 g |
| $(NH_4)_2SO_4$ | 0.18 g |
| $MgSO_4.7H_2O$ | 0.02 g |
| $FeCl_3(0.9725)$ | 0.1 ml |
| Fisons Trace Elements Mixture | 1 ml |
| Yeast Extract | 10 g |

The inoculated medium was shaken at a stirrer speed of 150 rpm at a temperature of 28° C. and a pH of 7. 200 ml of the inoculated medium were thereafter transferred to a fermenter having a 3 liter working volume and the medium set out in Table 1 was added. Cultivation then took place at a pH of 7 (maintained by additions of 50% ammonium hydoxide solution), a temperature of 25° C. and under a zero dissolved oxygen tension (DOT). A stirrer speed of 500 rpm was maintained during cultivation. During cultivation the glucose concentration in the medium was monitored and a further 200 g/l glucose was fed into the fermenter.

The product was found to contain 2.3 g/l of 2-deoxyuridine.

The 2-deoxyuridine produced was separated from the culture medium by ion exchange separation in the manner described below.

The cells were removed from the fermenter product using a centrifuge. The liquor containing 2-deoxyuridine was passed onto an adsorbent column (diameter 2.6 cm, length 50 cm) packed with SP207 resin (Mitsubishi Chemical Company, London, UK). The column was eluted with water pH7 at a flow rate of 4 column volumes per hour. A 2-deoxyuridine rich fraction was eluted after 3 column volumes had passed through the column.

EXAMPLE 3

Production of Strain 2.977

Strain 2.977 was produced by a two stage method from ATCC 19390.

In a first stage ATCC 19390 was treated with UV light and to the resulting culture was added the folate antagonist trimethoprim. Cells were selected which were resistant to trimethoprim producing strain No. 2.602. Strain No. 2.602 was thereafter cultured and treated with UV light and to the resulting culture was added 5-fluoro-2-deoxyuridine. Cells were selected which were resistant to high concentrations of 5-fluoro-2-deoxyuridine producing 2.977.

The production is essentially the same as that described earlier for strain L-17 (see Example 1).

I claim:

1. A process for the production of 2-deoxyuridine which comprises aerobically cultivating a 2-deoxyuridine producing bacterial strain of the species *Brevibacterium helvolum* in a culture medium containing an assimilable carbon source selected from the group consisting of sugars and alcohols and other nutrients under suitable cultural conditions, accumulating the produced 2-deoxyuridine directly in the medium and thereafter separating the produced and accumulated 2-deoxyuridine from the medium.

2. A process according to claim 1 wherein the strain is selected from the group consisting of *Brevibacterium helvolum* NCIMB 40117 and *Brevibacterium helvolum* NCIMB 40116.

3. A process according to claim 1 wherein the carbon source is glucose.

4. A process according to claim 1 wherein the strain is cultivated at a pH in the range 5 to 9.

5. A process according to claim 4 wherein the pH is in the range 6 to 8.

6. A process according to claim 1 wherein the strain is cultivated at a temperature in the range 20° to 35° C.

7. A process according to claim 6 wherein the temperature is in the range 25° to 30° C.

8. A process according to claim 1 wherein the 2-deoxyuridine is separated by adsorption onto an ion exchange resin and thereafter eluting it specifically from the resin with water.

* * * * *